US011116220B2

(12) United States Patent
Albright et al.

(10) Patent No.: US 11,116,220 B2
(45) Date of Patent: Sep. 14, 2021

(54) ANTIMICROBIAL COMPOSITIONS WITH ENHANCED EFFICACY

(71) Applicant: ECOLAB USA INC., Saint Paul, MN (US)

(72) Inventors: Jessica Albright, Saint Paul, MN (US); Daniel E. Pedersen, Saint Paul, MN (US); Cheryl A. Littau, Saint Paul, MN (US); Joseph R. Wegner, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 16/229,593

(22) Filed: Dec. 21, 2018

(65) Prior Publication Data

US 2019/0191704 A1 Jun. 27, 2019

Related U.S. Application Data

(60) Provisional application No. 62/609,603, filed on Dec. 22, 2017.

(51) Int. Cl.
| | | |
|---|---|---|
| *A01N 33/12* | (2006.01) | |
| *A01N 25/16* | (2006.01) | |
| *A01N 25/30* | (2006.01) | |
| *A01N 47/44* | (2006.01) | |
| *C11D 3/48* | (2006.01) | |
| *C11D 1/94* | (2006.01) | |
| *A61K 8/43* | (2006.01) | |
| *A61K 8/41* | (2006.01) | |
| *A61Q 19/10* | (2006.01) | |
| *A61K 8/04* | (2006.01) | |
| *C11D 1/62* | (2006.01) | |
| *C11D 1/75* | (2006.01) | |

(52) U.S. Cl.
CPC ............ *A01N 47/44* (2013.01); *A01N 25/16* (2013.01); *A01N 25/30* (2013.01); *A01N 33/12* (2013.01); *A61K 8/046* (2013.01); *A61K 8/416* (2013.01); *A61K 8/43* (2013.01); *A61Q 19/10* (2013.01); *C11D 1/94* (2013.01); *C11D 3/48* (2013.01); *C11D 1/62* (2013.01); *C11D 1/75* (2013.01)

(58) Field of Classification Search
CPC ......... A01N 33/12; A01N 25/16; A01N 25/30
See application file for complete search history.

(56) References Cited

U.S. PATENT DOCUMENTS

| | | | |
|---|---|---|---|
| 3,312,626 A * | 4/1967 | Hooker | C11D 17/006 510/150 |
| 4,144,326 A | 3/1979 | Luedicke, Jr. et al. | |
| 4,320,147 A | 3/1982 | Schaeufele | |
| 4,420,484 A | 12/1983 | Gorman et al. | |
| 5,389,685 A | 2/1995 | Smith et al. | |
| 5,403,579 A | 4/1995 | Michaels | |
| 5,534,265 A | 7/1996 | Fowler et al. | |
| 5,545,749 A | 8/1996 | Smith et al. | |
| 5,547,990 A | 8/1996 | Hall et al. | |
| 5,585,104 A | 12/1996 | Ha et al. | |
| 5,674,511 A | 10/1997 | Kacher et al. | |
| 5,753,245 A | 5/1998 | Fowler et al. | |
| 5,827,870 A | 10/1998 | Chodosh | |
| 5,833,741 A | 11/1998 | Walker | |
| 5,925,615 A | 7/1999 | Kern et al. | |
| 5,972,361 A | 10/1999 | Fowler et al. | |
| 5,980,931 A | 11/1999 | Fowler et al. | |
| 5,994,383 A | 11/1999 | Dyer et al. | |
| 6,008,177 A | 12/1999 | Sata et al. | |
| 6,022,551 A | 2/2000 | Jampani et al. | |
| 6,063,397 A | 5/2000 | Fowler et al. | |
| 6,066,611 A | 5/2000 | Ghosh et al. | |
| 6,071,866 A | 6/2000 | Fujiwara et al. | |
| 6,106,815 A | 8/2000 | Kang et al. | |
| 6,121,224 A | 9/2000 | Fonsny et al. | |
| 6,156,721 A | 12/2000 | Kwetkat et al. | |
| 6,287,546 B1 | 9/2001 | Reich et al. | |
| 6,300,508 B1 | 10/2001 | Raths et al. | |
| 6,464,764 B1 | 10/2002 | Lichtenberg et al. | |
| 6,488,948 B1 | 12/2002 | Danieli | |
| 6,495,122 B2 | 12/2002 | Fankauser et al. | |
| 6,518,229 B2 | 2/2003 | Tashjian et al. | |
| 6,525,071 B2 | 2/2003 | Dyer | |
| 6,583,181 B1 | 6/2003 | Chiang et al. | |
| 6,607,733 B1 | 8/2003 | Diec et al. | |
| 6,635,676 B2 | 10/2003 | Baker, Jr. et al. | |
| 6,890,895 B2 | 5/2005 | Oses et al. | |

(Continued)

FOREIGN PATENT DOCUMENTS

| | | |
|---|---|---|
| CA | 2701378 A1 | 10/2011 |
| CN | 101401774 A | 4/2009 |

(Continued)

OTHER PUBLICATIONS

Singh, PJ. New Product Development, 2016, Sulfate-Free for PC Applications, pp. 1-34.*
Edser, Caroline, "A Plethora of New Products", Focus on Surfactants, 2 pages, Jun. 2016.
Manzano, Sergio, "Surfactants with high compatibility and conditioning properties for new ecological formulation concepts", Focus: Natural Cosmetics, pp. 16-19, Jul. 2015.

(Continued)

*Primary Examiner* — Samira J Jean-Louis
(74) *Attorney, Agent, or Firm* — McKee, Voorhees & Sease, PLC

(57) ABSTRACT

The invention relates to antimicrobial compositions and methods of making the same. In particular, to antimicrobial hand wash compositions comprising an antimicrobial active and a primary foaming agent comprising a glucosamide. Preferred compositions further comprise a secondary foaming agent and a foam structure enhancing agent.

22 Claims, 1 Drawing Sheet

(56) References Cited

U.S. PATENT DOCUMENTS

| | | |
|---|---|---|
| 6,894,012 B2 | 5/2005 | Sebillotte-Amaud et al. |
| 6,939,840 B2 | 9/2005 | Lichtenberg et al. |
| 6,977,082 B2 | 12/2005 | Seitz, Jr. et al. |
| 7,015,180 B2 | 3/2006 | Coimbra et al. |
| 7,192,601 B2 | 3/2007 | Walker |
| 7,198,779 B2 | 4/2007 | Rifa Pinol et al. |
| 7,199,090 B2 | 4/2007 | Koivisto et al. |
| 7,303,744 B2 | 12/2007 | Wells et al. |
| 7,348,018 B2 | 3/2008 | McAtee et al. |
| 7,585,827 B2 | 9/2009 | Geary et al. |
| 7,589,051 B2 | 9/2009 | Erazo-Majewicz et al. |
| 7,754,770 B2 | 7/2010 | Curtis |
| 7,951,840 B2 | 5/2011 | Modak et al. |
| 7,993,630 B2 | 8/2011 | Gupta |
| 8,071,214 B2 | 12/2011 | Schwantes |
| 8,097,571 B2 | 1/2012 | Mellul et al. |
| 8,124,057 B2 | 2/2012 | Bosch et al. |
| 8,173,143 B2 | 5/2012 | Tecco et al. |
| 8,221,733 B2 | 7/2012 | Lichtenberg et al. |
| 8,309,111 B2 | 11/2012 | Fernandez de Castro et al. |
| 8,388,991 B2 | 3/2013 | Sondgeroth et al. |
| 8,491,877 B2 | 7/2013 | Schwartz et al. |
| 8,546,640 B2 | 10/2013 | Popovsky et al. |
| 8,574,561 B1 | 11/2013 | Patel et al. |
| 8,603,449 B2 | 12/2013 | Sunkel et al. |
| 8,603,550 B1 | 12/2013 | Fusco |
| 8,658,140 B2 | 2/2014 | Nguyen et al. |
| 8,673,274 B2 | 3/2014 | Schwartz et al. |
| 8,735,054 B1 | 5/2014 | Sun et al. |
| 9,017,652 B1 | 4/2015 | Askar et al. |
| 9,066,859 B1 | 6/2015 | Rizk et al. |
| 9,089,129 B2 | 7/2015 | Heisig et al. |
| 9,096,821 B1 | 8/2015 | Hope et al. |
| 9,150,318 B1 | 10/2015 | Sun et al. |
| 9,232,790 B2 | 1/2016 | Moen et al. |
| 9,259,006 B2 | 2/2016 | Lemons |
| 9,265,714 B2 | 2/2016 | Hardy et al. |
| 9,357,771 B2 | 6/2016 | Seidling et al. |
| 9,370,487 B2 | 6/2016 | Gurge et al. |
| 9,451,763 B2 | 9/2016 | Daigle et al. |
| 10,206,392 B2 | 2/2019 | Kloeppel et al. |
| 10,285,400 B2 | 5/2019 | Lei et al. |
| 2003/0022941 A1* | 1/2003 | Taylor ............... A01N 25/16 514/642 |
| 2003/0029812 A1 | 2/2003 | Burns et al. |
| 2003/0114342 A1 | 6/2003 | Hall |
| 2003/0147826 A1 | 8/2003 | Anthony et al. |
| 2003/0175333 A1 | 9/2003 | Shefer et al. |
| 2003/0187073 A1 | 10/2003 | Lichtenberg et al. |
| 2004/0052834 A1 | 3/2004 | West et al. |
| 2004/0220275 A1 | 11/2004 | Lutzeler et al. |
| 2004/0241114 A1 | 12/2004 | Gupta |
| 2005/0053634 A1 | 3/2005 | Ruppert et al. |
| 2005/0124723 A1 | 6/2005 | Fritschi et al. |
| 2005/0244346 A1 | 11/2005 | Nakao et al. |
| 2006/0134047 A1 | 6/2006 | Bakeev et al. |
| 2007/0065390 A1 | 3/2007 | Spengler et al. |
| 2007/0251029 A1 | 11/2007 | Bureiko et al. |
| 2007/0258918 A1 | 11/2007 | Modi |
| 2007/0264204 A1 | 11/2007 | Noor et al. |
| 2008/0275113 A1 | 11/2008 | Huetter et al. |
| 2009/0068122 A1 | 3/2009 | Pilch et al. |
| 2010/0227930 A1 | 9/2010 | Lusignan |
| 2011/0105604 A1 | 5/2011 | Sondgeroth et al. |
| 2011/0117032 A1 | 5/2011 | Gilding |
| 2012/0058151 A1 | 3/2012 | Gonzalez Ferreiro et al. |
| 2013/0053422 A1 | 2/2013 | Edmonds et al. |
| 2013/0233332 A1 | 9/2013 | Khenniche et al. |
| 2013/0280192 A1 | 10/2013 | Carter et al. |
| 2014/0005131 A1 | 1/2014 | Kroepke et al. |
| 2014/0100288 A1 | 4/2014 | DeSzalay |
| 2014/0134221 A1 | 5/2014 | Beyer et al. |
| 2014/0135245 A1 | 5/2014 | Annaheim et al. |
| 2014/0171490 A1 | 6/2014 | Gross et al. |
| 2014/0171512 A1 | 6/2014 | Kloeppel et al. |
| 2014/0178496 A1 | 6/2014 | Macoviak et al. |
| 2014/0378550 A1 | 12/2014 | Grundhofer |
| 2015/0073051 A1 | 3/2015 | Cohen et al. |
| 2015/0148425 A1 | 5/2015 | Fuls et al. |
| 2015/0272124 A1 | 10/2015 | Pedersen et al. |
| 2015/0313823 A1 | 11/2015 | Lockett et al. |
| 2016/0015731 A1 | 1/2016 | Ryoo et al. |
| 2016/0067152 A1 | 3/2016 | Franklin et al. |
| 2016/0074310 A1 | 3/2016 | Klug et al. |
| 2016/0106636 A1 | 4/2016 | Speaker et al. |
| 2016/0128944 A1 | 5/2016 | Chawrai et al. |
| 2016/0213001 A1 | 7/2016 | Parthasarathy et al. |
| 2017/0284605 A1 | 10/2017 | Janak et al. |
| 2020/0229435 A1 | 7/2020 | Malet et al. |
| 2020/0305437 A1 | 10/2020 | McGeechan et al. |

FOREIGN PATENT DOCUMENTS

| | | |
|---|---|---|
| CN | 101099714 B | 12/2010 |
| CN | 102018634 A | 4/2011 |
| CN | 102028625 A | 4/2011 |
| CN | 101684435 B | 6/2011 |
| CN | 101406441 B | 1/2012 |
| CN | 101953761 B | 6/2012 |
| CN | 101690701 B | 7/2012 |
| CN | 102716061 A | 10/2012 |
| CN | 102895151 B | 4/2014 |
| CN | 104086577 A | 10/2014 |
| CN | 104130415 A | 11/2014 |
| CN | 104188811 A | 12/2014 |
| CN | 103752211 B | 12/2015 |
| CN | 103251541 B | 1/2016 |
| CN | 103520032 B | 1/2016 |
| DE | 4443645 C2 | 8/1997 |
| DE | 19750245 A1 | 5/1999 |
| DE | 102007045242 A1 | 10/2008 |
| DE | 102013000586 B4 | 12/2014 |
| EP | 0422508 A2 | 4/1991 |
| EP | 0433911 A1 | 6/1991 |
| EP | 1043017 A2 | 10/2000 |
| EP | 0752846 B1 | 8/2001 |
| EP | 0821580 B1 | 8/2001 |
| EP | 0946129 B1 | 8/2001 |
| EP | 0952808 B1 | 8/2001 |
| EP | 1152741 B1 | 10/2006 |
| EP | 1683417 B1 | 3/2012 |
| EP | 1779896 B1 | 8/2012 |
| EP | 2594249 A2 | 5/2013 |
| EP | 2606934 A2 | 6/2013 |
| EP | 2664330 A1 | 11/2013 |
| EP | 2855651 B1 | 4/2015 |
| EP | 2720670 B1 | 10/2015 |
| EP | 2855647 B1 | 8/2016 |
| EP | 3241887 A1 | 11/2017 |
| FR | 3009954 B1 | 9/2015 |
| GB | 2405876 A | 3/2005 |
| IN | 3923CHE2012 | 3/2014 |
| JP | 2000191511 A | 7/2000 |
| JP | 2002325697 A | 11/2002 |
| JP | 2003300813 A | 10/2003 |
| JP | 3573061 B2 | 10/2004 |
| JP | 4151873 B2 | 9/2008 |
| JP | 4410903 B2 | 2/2010 |
| JP | 2010132612 A | 6/2010 |
| JP | 2010265214 A | 11/2010 |
| JP | 4892949 B2 | 3/2012 |
| JP | 2012171958 A | 9/2012 |
| JP | 5402613 B2 | 1/2014 |
| JP | 5625704 B2 | 11/2014 |
| JP | 5830324 B2 | 12/2015 |
| JP | 5971988 B2 | 8/2016 |
| KR | 101383779 B1 | 4/2014 |
| MX | 2012014003 A | 6/2014 |
| RU | 2252012 C1 | 5/2005 |
| WO | 9421771 A1 | 9/1994 |
| WO | 1994021226 A1 | 9/1994 |
| WO | 199747591 A1 | 12/1997 |
| WO | 9818447 A1 | 5/1998 |
| WO | 9827935 A1 | 7/1998 |

(56) References Cited

FOREIGN PATENT DOCUMENTS

| WO | 9838868 | A1 | 9/1998 |
|---|---|---|---|
| WO | 0035283 | A1 | 6/2000 |
| WO | 0059696 | A2 | 10/2000 |
| WO | 0121138 | A1 | 3/2001 |
| WO | 0121753 | A1 | 3/2001 |
| WO | 0162376 | A1 | 8/2001 |
| WO | 0185112 | A2 | 11/2001 |
| WO | 02064105 | A2 | 8/2002 |
| WO | 2007127330 | A2 | 11/2007 |
| WO | 2008049616 | A1 | 5/2008 |
| WO | 2009101409 | A1 | 8/2009 |
| WO | 2010018418 | A1 | 2/2010 |
| WO | 2012080224 | A2 | 6/2012 |
| WO | 2013178701 | A2 | 5/2013 |
| WO | 2013107586 | A2 | 7/2013 |
| WO | 2013178679 | A2 | 12/2013 |
| WO | 2014131870 | A1 | 9/2014 |
| WO | 2014131871 | A2 | 9/2014 |
| WO | 2014131872 | A2 | 9/2014 |
| WO | 2015143386 | A1 | 9/2015 |

OTHER PUBLICATIONS

Waidelich, Dr. M., "Discover Value. Discover GlucoTain", Clariant, PDF presentation, 28 pages, Apr. 15, 2015.

Ecolab USA INC., PCT/US2018/067198 filed Dec. 21, 2018, "The International Search Report and the Written Opinion of the International Searching Authority, or the Declaration", 17 pages, dated Mar. 25, 2019.

* cited by examiner

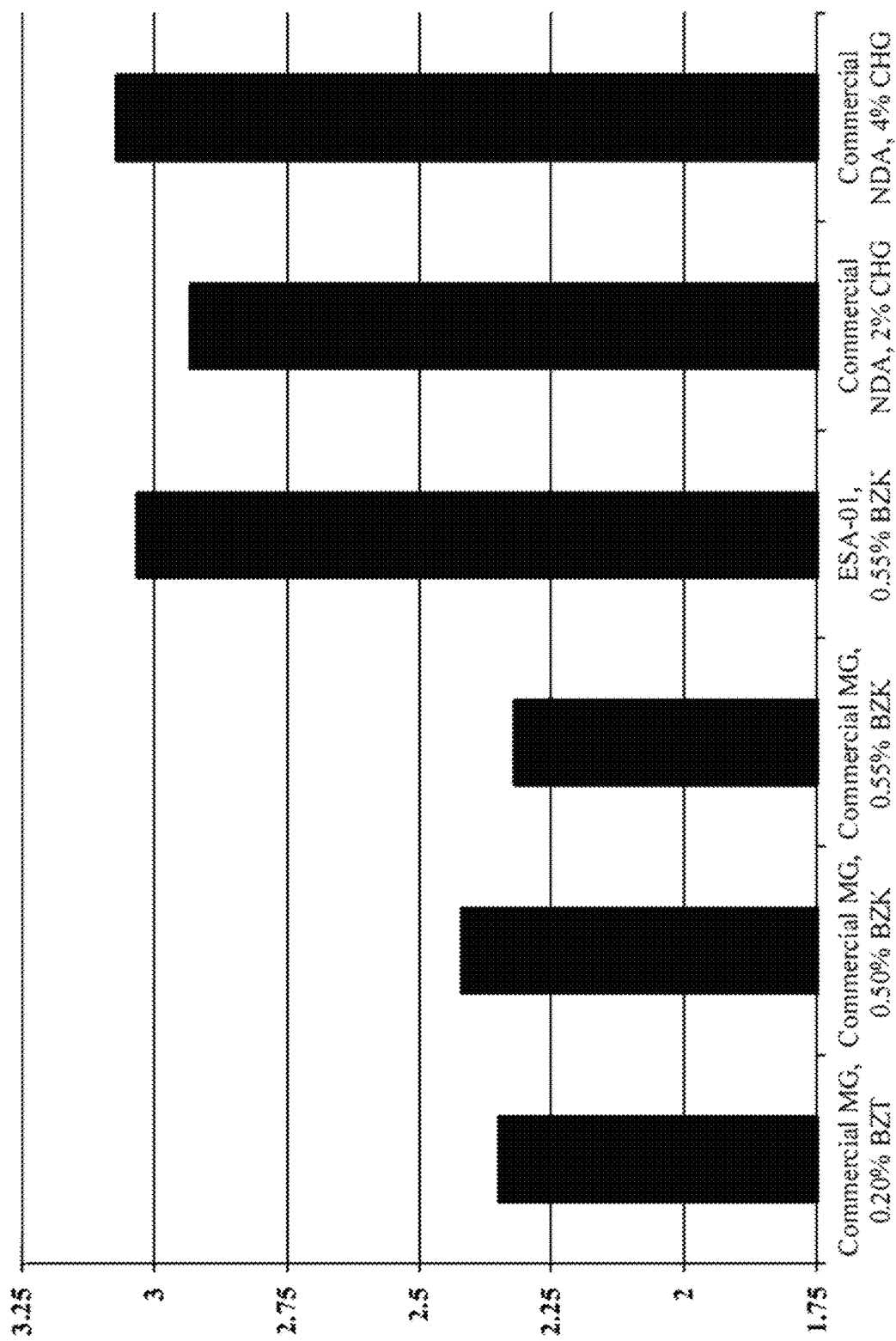

ANTIMICROBIAL COMPOSITIONS WITH ENHANCED EFFICACY

CROSS-REFERENCE TO RELATED APPLICATIONS

This application claims priority under 35 U.S.C. § 119 to Provisional Application U.S. Ser. No. 62/609,603 filed Dec. 22, 2017, herein incorporated by reference in its entirety.

FIELD OF THE INVENTION

The invention relates to antimicrobial compositions. In particular, to antimicrobial hand wash compositions.

BACKGROUND OF THE INVENTION

Antimicrobial hand soaps are an important component of maintaining public health by reducing the transfer of biological pathogens. Formulation of antimicrobial hand soaps is critical to ensure both acceptable user aesthetics including foam and feel during wash, as well as, the ability to reduce bacteria on skin. Moreover, the U.S. FDA is considering increasing the performance threshold required for antimicrobial soaps, by updating the passing requirements for the healthcare personnel hand wash method ASTM 1174. While some formulations may be able to meet these increased efficacy standards, many that may have sufficient antimicrobial efficacy are harsh on the skin, particularly if used repeatedly. An additional problem is that efficacious antimicrobial formulations can often have a deleterious effect on foaming properties, which are often desirable for hand washes. Further, new formulations, employing different antimicrobial compounds can often have unexpected interactions with other ingredients such that the compositions must be reformulated.

Traditional foaming agents are generally anionic surfactants. Amphoteric surfactants can be added to the primary anionic surfactant to increase foam height. Unfortunately, many commonly used foaming systems, particularly anionic surfactants, are incompatible with cationic active ingredients. Additionally, many surfactants may be chemically compatible with cationic active ingredients, but have a deleterious effect on the microbiologically efficacy of the active. Currently, most formulations of this type rely on amine oxide-type surfactants. While amine oxide surfactant systems can provide acceptable foaming characteristics with some level of bactericidal activity, current amine oxide-based systems don't possess sufficient microbiocidal activity to meet the new requirements being proposed by the FDA without a high level of active ingredient. Further, when amine oxide levels are increased, they can act as a skin irritant. This has made inclusion of amine oxides at a sufficient active concentration undesirable. Alternatives microbiocidal active components have also included chlorhexidene gluconate (CHG). Typical CHG systems require about 4% active concentration to achieve desired microbiocidal activity. This too can result in skin irritation.

Thus, new antimicrobial hand wash compositions are needed; particularly those that have increased antimicrobial efficacy and acceptable skin compatibility. Further, it has been found that formulating antimicrobial handwash compositions comprising a quaternary ammonium compound as an antimicrobial active with foaming surfactants that do not inhibit the cidal activity of the quaternary ammonium compound is critical to antimicrobial performance.

Accordingly, it is an objective of the claimed invention to provide antimicrobial compositions having increased antimicrobial efficacy.

A further object of the invention is to provide antimicrobial compositions that are dermally compatible with acceptable use aesthetics.

Yet another object of the invention is to provide antimicrobial compositions that have lower active concentrations of the microbiocidal component while maintaining or increasing antimicrobial efficacy.

Other objects, advantages and features of the present invention will become apparent from the following specification taken in conjunction with the accompanying FIGURE.

BRIEF SUMMARY OF THE PREFERRED EMBODIMENT

An advantage of the present antimicrobial compositions is that they provide improved antimicrobial efficacy while being dermally compatible. Yet another advantage of the antimicrobial compositions is that they maintain desired foaming properties while providing improved antimicrobial efficacy.

A preferred embodiment includes an antimicrobial composition comprising from about 0.01 wt. % to about 2 wt. % of an antimicrobial active compound comprising one or more of the following benzalkonium chloride, benzethonium chloride, chlorhexidine gluconate, didecyldimethyl ammonium chloride and mixtures thereof, wherein the antimicrobial active compound has antimicrobial activity toward Gram positive and/or Gram negative microorganisms; from about 0.1 wt. % to about 5 wt. % of a primary foaming agent, wherein the primary foaming agent comprises a glucosamide or a mixture of a glucosamide and a C8-C16 amine oxide derivative; and from about 65 wt. % to about 99.7 wt. % of a carrier; wherein the composition has a pH between about 5 and about 9.

A further preferred embodiment includes a dilutable antimicrobial composition comprising from about 0.3 wt. % to about 25 wt. % of an antimicrobial active compound comprising one or more of the following benzalkonium chloride, benzethonium chloride, chlorhexidine gluconate, and mixtures thereof, wherein the antimicrobial active compound has antimicrobial activity toward Gram positive and/or Gram negative microorganisms; from about 3 wt. % to about 50 wt. % of a primary foaming agent, wherein the primary foaming agent comprises a glucosamide or a mixture of a glucosamide and a C8-C16 amine oxide derivative; and optionally from about 0 wt. % to about 96.75 wt. % of a carrier; wherein the composition has a pH between about 5 and about 9.

Another preferred embodiment includes methods of preparing antimicrobial compositions in use and/or dilutable concentrations comprising mixing:

(a) an antimicrobial active compound comprising one or more of the following benzalkonium chloride, benzethonium chloride, chlorhexidine gluconate, didecyldimethyl ammonium chloride, and mixtures thereof, wherein the antimicrobial active compound has antimicrobial activity toward Gram positive and/or Gram negative microorganisms;

(b) a primary foaming agent, wherein the primary foaming agent comprises a glucosamide or a mixture of a glucosamide and a C8-C16 amine oxide derivative; and (c) optionally from about 0 wt. % to about 96.5 wt. % of a carrier;

(d) wherein the composition has a pH between about 5 and about 9.

While multiple embodiments of the antimicrobial compositions are disclosed, still other embodiments may become apparent to those skilled in the art from the following detailed description, which shows and describes illustrative embodiments of the invention. Accordingly, the detailed description, exemplary embodiments, and working examples are to be regarded as illustrative in nature and not restrictive.

BRIEF DESCRIPTION OF THE FIGURE

The FIGURE shows bar graph comparing the antimicrobial performance of an exemplary antimicrobial composition against various commercially available antimicrobial hand wash compositions. The FIGURE is representative of the data provided in Table 12 of Example 7.

The FIGURE contained herein is not a limitation on the various embodiments described herein and is purely exemplary of a preferred embodiment.

DETAILED DESCRIPTION OF THE PREFERRED EMBODIMENT

The embodiments of antimicrobial compositions are not limited to particular methods of preparation or use, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Use of the term antimicrobial "-cidal" effect or activity, refers to a lethal, irreversible action resulting in complete microbial cell destruction or incapacitation.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism or infective protein. Microorganisms include all prokaryotes. Microorganisms include bacteria (including cyanobacteria), spores, lichens, fungi, yeasts, protozoa, virinos, viroids, viruses, phages, and some algae. As used herein, the term "microbe" is synonymous with microorganism.

The term "surfactant" refers to a molecule having surface activity, including wetting agents, dispersants, emulsifiers, detergents, and foaming agents, and the like. It is understood to be inclusive of the use of a single surfactant or multiple surfactants.

The term "weight percent," "wt. %," "wt-%," "percent by weight," "% by weight," and variations thereof, as used herein, refer to the concentration of a substance as the weight of that substance divided by the total weight of the composition and multiplied by 100.

For the purpose of this patent application, successful microbial reduction is achieved when the microbial populations are reduced by at least about 0.5 log, or by significantly more than is achieved by a wash with water. Larger reductions in microbial population provide greater levels of protection.

As used herein, the term "soil" or "stain" refers to a non-polar oily substance which may or may not contain particulate matter such as mineral clays, sand, natural mineral matter, carbon black, graphite, kaolin, environmental dust, etc.

As used herein, the term "substantially free" refers to compositions completely lacking the component or having such a small amount of the component that the component does not affect the performance of the composition. The component may be present as an impurity or as a contaminant and shall be less than 0.1 wt-%. In another embodiment, the amount of the component is less than 0.05 wt-% and in yet another embodiment, the amount of component is 0 wt-%.

As used herein, the phrase "water soluble" means that the material is soluble in water in the present composition. In general, the material should be soluble at 25° C. at a concentration of between about 0.1 wt. % and about 15 wt. % of the water, more preferably at a concentration of between about 0.1 wt. % and about 10 wt. %.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, apparatuses, and compositions described herein may comprise, consist essentially of, or consist of the components and ingredients as well as other ingredients. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Compositions

Surprisingly the antimicrobial compositions described herein have been found to maintain or improve antimicrobial efficacy while being in active concentrations lower than many existing antimicrobial actives such as CHG. Additionally, the antimicrobial compositions described herein have been found to be dermally compatible and less irritating than existing products that provide the same level of microbiocidal efficacy.

Many surfactants inhibit the microbiological efficacy of cationic active ingredients such benzalkonium chloride, benzethonium chloride, and chlorhexidine gluconate. Thus, it has proven difficult to formulate cleaning compositions with cationic active ingredients that retain antimicrobial activity, provide adequate foaming characteristics, and possess acceptable skin compatibility. Moreover, as antimicrobial performance thresholds continue to be raised, the difficulty of formulating compositions meeting the performance requirements has become increasingly difficult. Thus, the compositions of the invention seek to solve these problems as well as other problems identified herein or others recognized in the art.

For example, amine oxides were also found to provide desired foaming and antimicrobial properties, but tend to be harsher on skin at higher concentrations. Thus, they can be employed, but it has been found that a lesser concentration can be preferred for embodiments with prolonged or repeated skin contact. Alkyl polyglucosides (APGs) were found to have moderate foaming and antimicrobial properties, but desired skin compatability. Betaines were found to provide desired foaming, poor antimicrobial properties, and moderate skin compatability. Based on these findings, it was determined that the primary foaming agent is preferably a glucamide, amine oxide, amine oxide derivative, or mixture thereof. Betaines and APGs can be included in the compositions in lesser concentrations, but are preferably absent from the compositions.

As demonstrated in the Examples contained herein, we have found that glucamides provide desired foaming, antimicrobial properties, and skin compatibility. The compositions can comprise an antimicrobial active compound, a carrier, and a primary foaming agent. In a preferred embodiment, the compositions can comprise an antimicrobial active compound, a carrier, a primary foaming agent, a secondary foaming agent, a chelant, and optionally one or more additional functional ingredients. In a more preferred embodiment, the compositions can comprise an antimicrobial active compound, a carrier, a primary foaming agent, a secondary foaming agent, a foam enhancing agent a chelant, an emollient, a preservative, and optionally one or more additional functional ingredients.

Unexpectedly it has been found that the primary foaming agents described herein can work in conjunction with the cationic active ingredients to provide desired foam properties while not inhibiting the antimicrobial properties. Moreover, some of the embodiments of the invention have been found to provide unexpected synergistic antimicrobial properties while maintaining foam properties and providing the desired skin compatibility and aesthetics.

Antimicrobial Active

The compositions comprise one or more antimicrobial active compounds, which have antimicrobial activity toward Gram positive and/or Gram negative microorganisms, including, preferably against *E. coli, S. marcescens*, and *S.*

*aureus* (MRSA). Preferred antimicrobial active compounds include: benzalkonium chloride, benzethonium chloride, chlorhexidine gluconate, didecyldimethylamonium chloride, and mixtures thereof.

Preferably, at use dilution the compositions comprise from about 0.01 wt-% to about 2 wt-% antimicrobial active, more preferably from about 0.05 wt-% to about 1.5 wt-% antimicrobial active, and most preferably from about 0.1 wt-% to about 1.0 wt-% antimicrobial active.

Preferably, in a concentrated composition, the antimicrobial active is in an amount between about 0.3 wt. % and about 25 wt. %, more preferably between about 0.5 wt. % and about 15 wt. %, and most preferably between about 1 wt. % and about 10 wt. %

In a preferred embodiment, the antimicrobial active contains less than 0.1 wt. % triclosan (2,4,4'-trichloro-2'hydroxy-diphenylether), preferably less than 0.05 wt. % triclosan, and most preferably is free of triclosan.

Carrier

The compositions comprise one or more carriers. Preferred carriers can include, but are not limited to, water and/or water-soluble carriers. Preferred water-soluble carriers include, but are not limited to, alcohols including ethanol, n-propanol, and isopropanol or mixtures thereof. In a preferred embodiment comprising water as a carrier, the water is deionized water or softened water.

The antimicrobial composition does not require a low pH or a high pH to provide a rapid reduction in microbial populations. Preferably the antimicrobial compositions have a pH of between about 3.5 and about 9, more preferably between about 4.5 and about 8, and most preferably between about 5.5 and about 7.5 Within this pH range, the antimicrobial compositions effectively reduce microbial populations, and are acceptable for dermal use.

Preferably, the use dilution compositions comprise from about 51 wt-% to about 99.7 wt-% carrier, more preferably from about 75 wt-% to about 99.5 wt-% carrier, and most preferably from about 80 wt-% to about 97.5 wt-% carrier.

Preferably, in a concentrated composition, the carrier is in an amount between about 0 wt. % and about 96.5 wt. %, more preferably between about 5 wt. % and about 94.5 wt. %, and most preferably between about 10 wt. % and about 91.5 wt. %

Primary Foaming Agent

The compositions comprise one or more primary foaming agents. Primary surfactants are responsible for the generation of foam volume. Preferred foaming agents include nonionic surfactants. Examples of nonionic primary surfactants include glucosamides and amine oxide derivatives. Both of these classes of surfactant provide adequate foam generation and do not have a significant negative impact on microbiological efficacy. In a preferred embodiment, the compositions comprise one or more primary foaming agents.

Preferred glucosamides are those having less than 18 carbons in the alkyl chain. More preferred are C8-C16 glucosamides which include, but are not limited to, caprylloyl/caproyl methyl glucosamide, cocoyl methyl glucosamide, lauroyl/myristoyl methyl glucosamide, and mixtures thereof. Most preferred are glucosamides having between about 10 and about 14 carbons in the alkyl chain. A preferred glucosamide is lauroyl methyl glucamide as shown in the formula below:

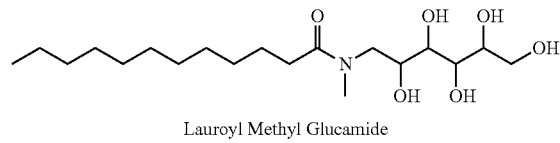 [SMILES: CCCCCCCCCCCC(=O)N(C)CC(O)C(O)C(O)C(O)CO]

Lauroyl Methyl Glucamide

One surprising finding is that while glucosamides are suitable for the compositions, structurally similar surfactants such as widely used C8-C18 glucosides are not suitable. C8-C18 glucosides were found to have a detrimental effect on microbiological efficacy. This is demonstrated in Example 1 in this disclosure. The inhibitory effect observed with C8-C18 glucosides, and the lack of a similar inhibitory effect with the C8-C18 glucosamide surfactants is surprising due to the high degree of structural similarity. The polar head group of the glucoside and glucosamide classes of surfactants are shown below. Head groups are depicted in their ring open state.

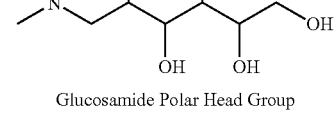

Glucoside Polar Head Group

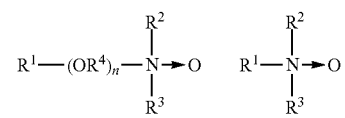

Glucosamide Polar Head Group

The primary foaming surfactant can also comprise an alkyl amine oxide or alkyl ether amine oxide, hereto referred to a amine oxides. Amine oxides are a semi-polar type of nonionic surface active agents composed of tertiary amine oxides corresponding to the general formulas:

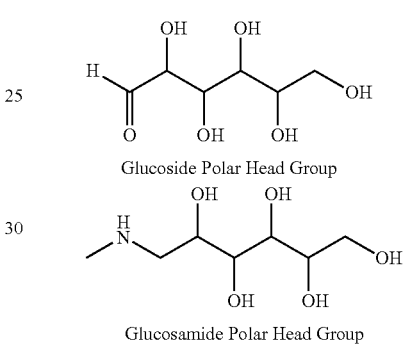

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene, a hydroxyalkylene group, or a alkylether group, containing 2 to 3 carbon atoms; and n ranges from 0 to about 20. An amine oxide can be generated from the corresponding amine and an oxidizing agent, such as hydrogen peroxide. If an amine oxide is included in the composition, it is preferably a C8-18 amine oxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

The compositions preferably comprise a glucosamide or a mixture of a glucosamide and amine oxide. Preferably the primary foaming agent has a ratio of glucosamide to amine oxide between about 100:0 (where there is no amine oxide) to about 50:50. In an embodiment where there is a mixture of glucosamide and amine oxide, preferably the ratio of glucosamide to amine oxide is between about 90:10 and about 50:50, more preferably between about 90:10 and about 60:40, even more preferably between about 90:10 and about 70:30.

The compositions of the invention can comprise the primary foaming agent in a concentration of between about 0.5 wt. % and about 8 wt. %, preferably about 1 wt. % and about 6 wt. %, and more preferably between about 1 wt. % and about 4 wt. %. In a concentrated composition, the primary foaming agent can be in an amount between about 3 wt. % and about 50 wt. %, preferably between about 4 wt. % and about 45 wt. %, more preferably between about 5 wt. % and about 40 wt. %.

While amine oxides are often employed in dermal cleansers, it is preferred that they only be used in a small amount in these compositions due to their defatting properties, which can cause skin irritation and dryness. As such, in preferred embodiments, the antimicrobial compositions can be substantially free of an amine oxide surfactant or contain less than about 3 wt. %; more preferably, less than about 2 wt. %; still more preferably; less than about 1.5 wt. %, even more preferably; less than about 1 wt. %; yet more preferably less than about 0.5 wt. %; and most preferably less than about 0.1 wt. %.

Secondary Foaming Agent

The compositions comprise one or more secondary foaming agents. Preferred foaming agents, include, amphoteric surfactants, nonionic surfactants, and cationic surfactants. In a preferred embodiment, the compositions comprise one or more secondary foaming agents; in a more preferred embodiment the compositions comprise two or more secondary foaming agents. Suitable secondary foaming agents are discussed below.

The compositions of the invention can comprise the secondary foaming agent in a concentration of between about 0.1 wt. % and about 5 wt. %, preferably about 0.5 wt. % and about 4 wt. %, and more preferably between about 1 wt. % and about 2.5 wt. %. In a concentrated composition, the secondary foaming agent can be in an amount between about 1 wt. % and about 30 wt. %, preferably between about 4 wt. % and about 25 wt. %, more preferably between about 8 wt. % and about 20 wt. %.

Cationic Surfactants

Examples of cationic surfactants suitable as foaming agents include, but are not limited to, quaternized polysaccharides, alkyl polysaccharides, alkoxylated amines, alkoxylated ether amines, and mixtures thereof.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution. At pH levels less than 4, amine oxide type surfactants can also have some cationic character.

The simplest cationic amines, amine salts and quaternary ammonium compounds can be schematically drawn thus:

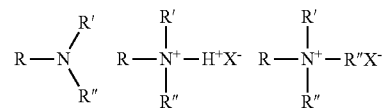

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Examples of cationic surfactants includes the chloride, bromide, or methosulfate salts of alkyltrimethylammonium species where the alkyl group chain length is C8-C18, the preferred alkyl chain length is C8-16, and the most preferred alkyl chain length is C8-C14.

Nonionic Surfactants

Examples of nonionic surfactants suitable as foaming agents include, but are not limited to, alcohol ethoxylates, fatty acid ethoxylates, alkyl phenol ethoxylate, monoalkonaolamide ethoxylates, sorbitan esters and their ethoxylated derivatives, ethoxylated fats and oils, amine ethoxylates, ethylene oxide-propylene oxide co-polymers, glycol esters, glycerol and polyglycerol esters, sucrose esters mono and polysaccharides surfactants, such as alkyl polyglucosides.alkyl alcohol ethoxylates, capped alkyl alcohol ethoxylates, fatty alcohol ethoxylate propoxylates, ethoxylated siloxane copolymers (PEG dimethicone) including alkyl capped, PEG/PPG dimethicones, mixtures thereof, or the like. Preferred substituted amides include, but are not limited to, glucosamides.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties.

Phospholipids and Phospholipid Derivatives

Phospholipid and/or phospholipid derivative surfactants can also be included. Preferred phospholipid derivatives include, but are not limited to, diester and triester phosphatides with multiple chain groups, and mixtures thereof. Preferred phospholipid surfactants include, but are not limited to coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Commercially prominent imidazoline-derived amphoterics that can be employed in the present compositions include for example: Cocoamphopropionate, Cocoamphocarboxypropionate, Cocoamphoglycinate, Cocoamphocarboxyglycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na$)$_2$—$CH_2$—$CH_2$—OH or $C_{12}$-alkyl-C(O)—N(H)—$CH_2$—$CH_2$—$N^+$($CH_2$—$CO_2Na$)$_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

For example, the compositions can include cocoamido propyl betaine, however, the level of betaine in the system can have a negative impact on efficacy requiring additional active ingredient to compensate for efficacy. Due to this interaction, the amount of betaine in the system is preferably less than 1%, more preferably less than 0.5%, and most preferably free of betaine.

Preferred secondary foaming agents include, lauryl trimethyl ammonium chloride, palmitamidopropyl trimonium chloride, diester phosphatides with multiple chain groups, triester phosphatides, coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof.

Preferably, the compositions comprise from about 0.1 wt-% to about 5 wt-% foaming agent, more preferably from about 0.5 wt-% to about 4.5 wt-% foaming agent, and most preferably from about 1.5 wt-% to about 4 wt-% foaming agent.

Chelants

The compositions can optionally comprise one or more chelants. Preferred chelants, include, but are not limited to, phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelants include nitroloacetates and their derivatives, and mixtures thereof.

Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA), including its various salts; N-hydroxyethyl-ethylenediaminetriacetic acid (HEDTA); diethylenetriaminepentaacetic acid (DTPA); and alanine-N,N-diacetic acid; and methylglycine diacetic acid (MGDA); n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms.

Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelants include polyaspartic acid or co-condensates of aspartic acid with other amino acids, $C_4$-$C_{25}$-mono-or-dicarboxylic acids and $C_4$-$C_{25}$-mono-or-diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

Preferred chelants include, EDTA, MGDA, and NTA. Most preferred chelants include EDTA and MGDA.

The addition of a chelant in antimicrobial compositions can provide increased efficacy against gram negative microorganisms. Surprisingly, however, it was found that certain chelating agents provided substantially increased efficacy against gram negative microorganisms while others provided little to no improvement. Glutamic acid diacetic acid (GLDA) is an amino acid-based chelating agent. It is well-known for its ability to boost the efficacy of biocides across a wide variety of formulation types, including personal care products. Surprisingly, the addition of GLDA to a base formula did not show any enhancement of antimicrobial efficacy. Methylglycinediacetic acid (MGDA), like GLDA, is an amino acid-containing chelating agent. Their structures are shown below:

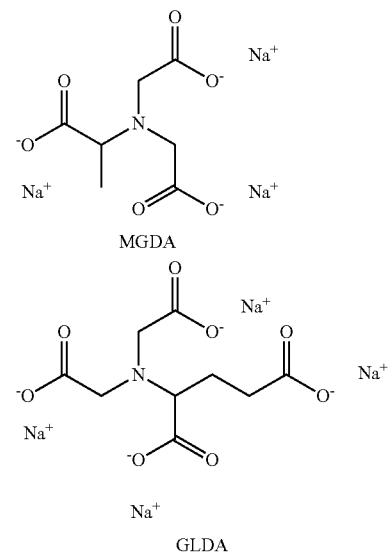

MGDA

GLDA

Despite the structural similarities of these two compounds, the functional effect of the two compounds vary drastically. The addition of MGDA was found to significantly enhance the biocidal activity of the cationic active-containing base formula.

Traditional chelating agents, including EDTA, were also shown to have a positive impact on microbiological efficacy, particularly against gram negative organisms.

In a preferred use dilution embodiment, the compositions can comprise from about 0.01 wt-% to about 1 wt-% chelant, more preferably from about 0.05 wt-% to about 0.5 wt-% chelant, and most preferably from about 0.1 wt-% to about 0.4 wt-% chelant.

In a preferred concentrated embodiment, the compositions can comprise from about 0.1 wt-% to about 10 wt-% chelant, more preferably from about 0.5 wt-% to about 5 wt-% chelant, and most preferably from about 1 wt-% to about 4 wt-% chelant.

Foam Structure Enhancing Agent

In preferred embodiments, the compositions can comprise one or more foam structure enhancing agents. Foam structure enhancing agents are agents that change the physical foam structure including foam stability, bubble size, density and rigidity thereby imparting sensorial attributes during the washing process. Users may describe such sensorial attributes as lather, creaminess, cushion, and/or slip. Preferred foam structure enhancing agents, include, but are not limited to, hexylene glycol, polyols, such as glycerol (glycerin), propylene glycol, hexylene glycol, diethylene glycol, propylene glycol n-alkanols, ethylene glycol, polyethylene glycols, other glycols and mixtures thereof.

Preferably, the compositions can comprise from about 0.05 wt-% to about 4 wt-% foam structure enhancing agent, more preferably from about 0.5 wt-% to about 3 wt-% foam structure enhancing agent, and most preferably from about 1 wt-% to about 2 wt-% foam structure enhancing agent. In a concentrated formulation, the foam structure enhancing agent is preferably in an amount between about 0.5 wt. % and about 40 wt. %, more preferably between about 1 wt. % and about 30 wt. %, most preferably between about 1 wt. % and about 10 wt. %.

In a preferred embodiment a novel foam structure agent is disclosed as a linear, non-substituted high molecular weight polyethylene glycol, such as PEG 300 or greater, or PEG 1000 or greater. In a particularly preferred embodiment the PEG 8000 is the foam structure enhancing agent.

Examples of other foam structure enhancing agents include an organic solvent, other than a short chain alcohol, typically soluble in both water and oil. Examples of foam structure enhancing agents according to the present invention include: polyols, such as glycerol (glycerin), propylene glycol, hexylene glycol, diethylene glycol, propylene glycol n-alkanols, ethylene glycol, other glycols, monooleate of ethoxylated glycerides (with 8 to 10 ethylene oxide units); esters, such as isopropyl myristate/palmitate, myristyl alcohol, lauryl alcohol, lauryl lactate, amides, such as acetamide oleates such as triolein; According to one preferred embodiment the foam stabilizer is hexylene glycol.

The foam structure enhancing agents constituent may also comprise at least one a fatty alkanolamide, examples of which include but are not limited to: cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof. Alkanol amides may provide an ancillary thickening benefit as well. A preferred alkanol amide is diisopropanolamide, such as the Cola® liquid non-DEA amides available from Colonial chemical which includes cocamide DIPA (diisopropanolamide), Soyamide DIPA, lauramide DIPA, or myristamide DIPA. In a preferred embodiment the composition is substantially free of DEA and/or MEA, such as in cocamide DEA.

In yet another preferred embodiment the composition includes diisopropanolamide as a part of the foam structure enhancing component. Diisopropanolamide may be present in the entire composition in an amount of from about 0.01 wt. % to about 8 wt. %, from about 0.05 wt. % to about 5 wt. % and more preferably from about 0.1 wt. % to about 3 wt. %.

Additional foam structure enhancing agents may include agents that modify slip during the hand washing process by helping the foam structure enhancing agents to flow more easily and more smoothly in the hand of a user. Examples of these agents may include; caprylyl glycol, ethylhexyl glycerine and phenoxyethanol. According to one preferred embodiment the foam structure enhancing agent is phenoxyethanol. Phenoxyethanol is often recognized as a preservative; however, it was surprisingly found that it acted as an excellent foam structure enhancing agent. The slip modifying agent is present in the composition in an amount from about 0.05 wt. % to about 10 wt. %, preferably from about 0.1 wt. % to about 7 wt. %.

Additional Ingredients

The antimicrobial compositions can include additional optional components. Often these components are added for functional benefits and/or properties. As such, in some embodiments, the antimicrobial composition including the antimicrobial active component, foaming surfactant, and carrier may provide a large amount, or even all of the total weight of the antimicrobial composition, for example, in embodiments having few or no additional functional materials disposed therein. The functional ingredients provide desired properties and functionalities to the antimicrobial composition. For the purpose of this application, the term "functional ingredients" include ingredients that when dispersed or dissolved in a use and/or concentrate solution, such as an aqueous solution, provide a beneficial property in a particular use. The antimicrobial compositions can optionally contain other disinfectants, dyes, emollients, fragrances, pH modifiers, preservatives, sanitizers, surfactants, and thickening or gelling agents. Some particular examples of additional functional ingredients are discussed in more detail below, but it should be understood the particular ingredients discussed below are given by way of example only, and that a broad variety of other functional ingredients may be used. For example, may of the functional material discussed below relate to materials used in disinfecting and/or cleansing applications, but it should be understood that other embodiments may include functional materials for use in other applications.

Dye

The composition may optionally include a dye. Examples of dyes include any water soluble or product soluble dye, any FD&C or D&C approved dye.

Emollient

The compositions can optionally comprise one or more emollients. Preferred emollients, include, but are not limited to, capric/caprylic triglyceride, C12-15 alkyl benzoate, capric triglyceride, caprylic triglyceride, isopropyl myristrate, isopropyl palmitate, octyldodecanol, decyl oleate, cocoglycerides, ethylhexyl stearate, ceteraryl isononanoate, cetearyl ethyhexanonate, decyl cocoate, cetyl dimethicone, ethylhexyl palmitate, PPG-11 stearyl ether, PPG-15 stearyl ether, PPG-14 butyl ether, dicaprylyl carbonate, dibutyl adipate, hexyl laurate, dicaprylyl ether, propylheptyl caprylate, isocetyl palmitate, hydrogentated polyisobutene, diethylhexylcarbonate, tocopheryl acetate, methyl gluceth-10, methyl gluceth-20, dicaprylyl carbonate, dibutyl adipate, hexyl laurate, dicaprylyl ether, propylheptyl caprylate, ethoxylated natural and synthetic oils, and mixtures thereof. Preferred emollients, include, but are not limited to, C12-15 alkyl benzoate, capric triglyceride, caprylic triglyceride, isopropyl myristrate, isopropyl palmitate, octyldodecanol, decyl oleate, cocoglycerides, ethylhexyl stearate, ceteraryl isononanoate, cetearyl ethyhexanonate, decyl cocoate, cetyl dimethicone, ethylhexyl palmitate, PPG-11 stearyl ether, PPG-15 stearyl ether, PPG-14 butyl ether, and mixtures thereof.

When an emollient is included in the use dilution compositions, it is preferably in an amount from about 0.01 wt-% to about 1 wt-%, more preferably from about 0.05 wt-% to about 0.75 wt-%, and most preferably from about 0.1 wt-% to about 0.5 wt-%.

When an emollient is included in the concentrated compositions, it is preferably in an amount from about 0 wt-% to about 10 wt-%, more preferably from about 0.5 wt-% to about 7.5 wt-%, and most preferably from about 1 wt-% to about 5 wt-%.

Fragrance

The antimicrobial compositions can optionally comprise a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

Preferably, in a use dilution composition, the fragrance is in a concentration between about 0 wt. % and about 1 wt. %, more preferably between about 0.01 wt. % and about 0.5 wt. %.

Preferably, in a concentrated composition, the fragrance is in a concentration betwee about 0 wt. % and about 10 wt. %, more preferably between about 0.1 wt. % and about 10 wt. %.

Humectant

In preferred embodiments, the compositions can comprise one or more humectants. Preferred humectants, include, but are not limited to, hydroxyethyl urea, agarose, urea, sodium PCA, arginine PCA, fructose, glucose, glutamic acid, glycerin, honey, lactose, maltose, polyethylene glycol, sorbitol, polyquats and mixtures thereof.

Preferably, the use dilution compositions can comprise from about 0 wt-% to about 3 wt-%, 0.05 wt-% to about 3 wt-% humectant, more preferably from about 0.1 wt-% to about 5 wt-% humectant, and most preferably from about 0.3 wt-% to about 1 wt-% humectant.

Preferably, the concentrated compositions can comprise from about 3 wt-% to about 30 wt-% humectant, more preferably from about 3 wt-% to about 15 wt-% humectant, and most preferably from about 3 wt-% to about 10 wt-% humectant.

Preservative

In a preferred embodiment, the compositions comprise one or more preservatives. Preferred preservatives, include, phenolics, halogen compounds, metal derivatives, amines, alkanolamines, nitro derivatives, biguanides, analides, organosulfur and sulfur-nitrogen compounds, alkyl parabens, and other compounds.

Preferred phenolic compounds include, but are not limited to, pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof.

Preferred halogen compounds include, but are not limited to iodine-poly(vinylpyrrolidin-onen) complexes, and bromine compounds such as 2-bromo-2-nitropropane-1,3-diol, and derivatives thereof.

Preferred amines and nitro containing compounds include, but are not limited to, hexahydro-1,3,5-tris(2-hydroxyethyl)-s-triazine, dithiocarbamates such as sodium dimethyldithiocarbamate, and derivatives thereof.

Preferred biguanides include, but are not limited to, polyaminopropyl biguanide and chlorhexidine gluconate.

Preferred alkyl parabens include, but are not limited to, methyl, ethyl, propyl and butyl parabens.

Other optional preservatives include, but are not limited to, benzoic acid, sorbic acid, triclosan chloroxylenol (parachloro meta-xylenol), caprylyl glycol, glycerol caprylate, ethylhexyl glycerin, benzoates, sorbates, or mixtures thereof.

When a preservative is included in the use dilution compositions, it is preferably in an amount from about 0.01 wt-% to about 2 wt-%, more preferably from about 0.1 wt-% to about 1.5 wt-%, and most preferably from about 0.2 wt-% to about 1 wt-%.

When a preservative is included in the concentrated compositions, it is preferably in an amount from about 0.1 wt-% to about 20 wt-%, more preferably from about 1 wt-% to about 15 wt-%, and most preferably from about 2 wt-% to about 10 wt-%.

Thickeners

The composition may optionally include a thickener. Examples of compatible thickeners include Guar, Hydroxypropyl Guar, Xanthan, Carrageenan, Karaya, Polyethylene Glycol (PEG), Cellulose Derivatives, including but not limited to hydroxyethyl cellulose, hydroxypropyl cellulose, hydroxylpropylmethtyl cellulose, alkyl modified hydroxyethyl cellulose, hydroxylethylpropyl, polyquaternium 10, Associative Thickeners including but not limited to hydrophobically modified ethoxylated urethanes (HEUR), polyethylene glycol dialkyl esters, PEG/PPG-450/50 trimethylolpropane dodecyl ether, Bis-C16-20 Isoalkoxy TMHDI/PEG-90 Copolymer, PEG-120 Methyl Glucose dioleate, PEG-18 Glceryl olieate/cocoate, sorbitan sesquicaprylate, and mixtures thereof.

Exemplary Embodiments of the Antimicrobial Compositions

The antimicrobial compositions can be prepared as a ready-to-use solution or a concentrated dilutable composition.

Exemplary ready-to-use compositions are provided in Tables 1A through 1F. The ranges in each table should be considered to be modified by the word "about" as defined herein.

TABLE 1A

| Ingredients | First Exemplary Embodiment (wt. %) | Second Exemplary Embodiment (wt. %) | Third Exemplary Embodiment (wt. %) |
|---|---|---|---|
| Antimicrobial Active | 0.01-2 | 0.05-1.5 | 0.1-1 |
| Primary Foaming Agent | 0.1-5 | 0.5-4.5 | 1.5-4 |
| Carrier | 65-99.7 | 75-99.5 | 80-95 |

TABLE 1B

| Ingredients | First Exemplary Embodiment (wt. %) | Second Exemplary Embodiment (wt. %) | Third Exemplary Embodiment (wt. %) |
|---|---|---|---|
| Antimicrobial Active | 0.01-2 | 0.05-1.5 | 0.1-1 |
| Primary Foaming Agent | 0.1-5 | 0.5-4.5 | 1.5-4 |
| Carrier | 65-99.7 | 75-99.5 | 80-95 |
| Foam Structure Enhancing Agent | 0.05-4 | 0.5-3 | 1-2 |
| Humectant | 0.05-3 | 0.1-1.5 | 0.3-1 |
| Additional Optional Ingredients | 0-15 | 0-15 | 0.01-15 |

TABLE 1C

| Ingredients | First Exemplary Embodiment (wt. %) | Second Exemplary Embodiment (wt. %) | Third Exemplary Embodiment (wt. %) |
|---|---|---|---|
| Antimicrobial Active | 0.01-2 | 0.05-1.5 | 0.1-1 |
| Primary Foaming Agent | 0.1-5 | 0.5-4.5 | 1.5-4 |
| Carrier | 65-99.7 | 75-99.5 | 80-95 |
| Foam Structure Enhancing Agent | 0.05-4 | 0.5-3 | 1-2 |
| Humectant | 0.05-3 | 0.1-1.5 | 0.3-1 |
| Chelant | 0.01-1 | 0.05-0.5 | 0.1-0.4 |
| Emollient | 0-1 | 0.05-0.75 | 0.1-0.5 |
| Preservative | 0.01-2 | 0.1-1.5 | 0.2-1 |
| Fragrance | 0-1 | 0-1 | 0.01-1 |
| Additional Optional Ingredients | 0-15 | 0-15 | 0.01-10 |

TABLE 1D

| Ingredients | First Exemplary Embodiment (wt. %) | Second Exemplary Embodiment (wt. %) | Third Exemplary Embodiment (wt. %) |
|---|---|---|---|
| Benzalkonium Chloride | 0.01-2 | 0.05-1.5 | 0.1-1 |
| Primary Foaming Agent | 0.1-5 | 0.5-4.5 | 1.5-4 |
| Secondary Foaming Agent | 0.1-5 | 0.5-4 | 1-2.5 |
| Carrier | 65-99.7 | 75-99.5 | 80-95 |
| Foam Structure Enhancing Agent | 0-4 | 0.1-3 | 1-2 |
| Humectant | 0-3 | 0.05-1.5 | 0.1-1 |
| Chelant | 0-1 | 0.05-0.5 | 0.1-0.4 |
| Emollient | 0-1 | 0.05-0.75 | 0.1-0.5 |
| Preservative | 0-2 | 0.1-1.5 | 0.2-1 |
| Fragrance | 0-1 | 0-1 | 0.01-1 |
| Additional Optional Ingredients | 0-15 | 0-15 | 0.01-10 |

TABLE 1E

| Ingredients | First Exemplary Embodiment (wt. %) | Second Exemplary Embodiment (wt. %) | Third Exemplary Embodiment (wt. %) |
|---|---|---|---|
| Benzethonium Chloride | 0.01-2 | 0.05-1.5 | 0.1-1 |
| Primary Foaming Agent | 0.1-5 | 0.5-4.5 | 1.5-4 |
| Secondary Foaming Agent | 0.1-5 | 0.5-4 | 1-2.5 |
| Carrier | 65-99.7 | 75-99.5 | 80-95 |
| Foam Structure Enhancing Agent | 0-4 | 0.1-3 | 1-2 |
| Humectant | 0-3 | 0.05-1.5 | 0.1-1 |
| Chelant | 0-1 | 0.05-0.5 | 0.1-0.4 |
| Emollient | 0-1 | 0.05-0.75 | 0.1-0.5 |
| Preservative | 0-2 | 0.1-1.5 | 0.2-1 |
| Fragrance | 0-1 | 0-1 | 0.01-1 |
| Additional Optional Ingredients | 0-15 | 0-15 | 0.01-10 |

TABLE 1F

| Ingredients | First Exemplary Embodiment (wt. %) | Second Exemplary Embodiment (wt. %) | Third Exemplary Embodiment (wt. %) |
|---|---|---|---|
| Chlorhexidene Gluconate | 0.01-2 | 0.05-1.5 | 0.1-1 |
| Primary Foaming Agent | 0.1-5 | 0.5-4.5 | 1.5-4 |
| Secondary Foaming Agent | 0.1-5 | 0.5-4 | 1-2.5 |
| Carrier | 65-99.7 | 75-99.5 | 80-95 |
| Foam Structure Enhancing Agent | 0-4 | 0.1-3 | 1-2 |
| Humectant | 0-3 | 0.05-1.5 | 0.1-1 |
| Chelant | 0-1 | 0.05-0.5 | 0.1-0.4 |
| Emollient | 0-1 | 0.05-0.75 | 0.1-0.5 |
| Preservative | 0-2 | 0.1-1.5 | 0.2-1 |
| Fragrance | 0-1 | 0-1 | 0.01-1 |
| Additional Optional Ingredients | 0-15 | 0-15 | 0.01-10 |

Additionally, the antimicrobial concentrations can be prepared in the format of a liquid or gel concentrate, which would be subsequently diluted to the proper use concentration with a carrier either manually or by suitable equipment or an apparatus. Preferably concentrated liquid compositions are between 2 to 10 times the concentration of the ready-to-use formulations ingredients, except the carrier.

In one embodiment, the antimicrobial compositions can be provided as a liquid concentrate such that the antimicrobial composition is substantially free of any added carrier, or the concentrate may contain a nominal amount of carrier. The concentrate can be formulated without any carrier or can be provided with a relatively small amount of carrier in order to reduce the expense of transporting the concentrate.

Embodiments of concentrated compositions can be concentrated sufficiently to be diluted with a carrier (preferably comprising water) at a ratio of between about 1:1 and about 1:15. A concentrated composition that will be diluted at a ratio of about 1:15 will likely be substantially free of any added carrier. Other suitable dilution ratios include about 1:2, about 1:3, about 1:4, about 1:5, about 1:6, about 1:7, about 1:8, about 1:9, about 1:10, about 1:11, about 1:12, about 1:13, and about 1:14.

When provided as a liquid or gel concentrate composition, the concentrate can be diluted through dispensing equipment using aspirators, peristaltic pumps, gear pumps, mass flow meters, and the like. This liquid or gel concentrate embodiment can also be delivered in bottles, jars, dosing bottles, bottles with dosing caps, and the like. The liquid or gel concentrate composition can be filled into a multi-chambered cartridge insert that is then placed in a spray bottle or other delivery device filled with a pre-measured amount of water.

Exemplary concentrated compositions are provided in Tables 2A through 2G.

TABLE 2A

| Ingredients | First Exemplary Embodiment (wt. %) | Second Exemplary Embodiment (wt. %) | Third Exemplary Embodiment (wt. %) |
| --- | --- | --- | --- |
| Antimicrobial Active | 0.3-25 | 0.5-15 | 1-10 |
| Primary Foaming Agent | 3-50 | 5-45 | 7.5-40 |
| Carrier | 25-96.5 | 40-94.5 | 50-91.5 |

TABLE 2B

| Ingredients | First Exemplary Embodiment (wt. %) | Second Exemplary Embodiment (wt. %) | Third Exemplary Embodiment (wt. %) |
| --- | --- | --- | --- |
| Antimicrobial Active | 0.3-25 | 0.5-15 | 1-10 |
| Primary Foaming Agent | 3-50 | 4-45 | 5-40 |
| Carrier | 10-90 | 20-90 | 50-90 |
| Foam Structure Enhancing Agent | 0.5-40 | 1-30 | 1-10 |
| Humectant | 3-30 | 3-15 | 0.3-1 |
| Additional Optional Ingredients | 0-30 | 0-30 | 0.01-30 |

TABLE 2C

| Ingredients | First Exemplary Embodiment (wt. %) | Second Exemplary Embodiment (wt. %) | Third Exemplary Embodiment (wt. %) |
| --- | --- | --- | --- |
| Antimicrobial Active | 0.3-25 | 0.5-15 | 1-10 |
| Primary Foaming Agent | 3-50 | 4-45 | 5-40 |
| Carrier | 5-90 | 10-90 | 40-90 |
| Foam Structure Enhancing Agent | 0.5-40 | 1-30 | 1-10 |
| Humectant | 3-30 | 3-15 | 3-10 |
| Chelant | 0.1-10 | 0.5-5 | 1-4 |
| Emollient | 0-10 | 0.5-7.5 | 1-5 |
| Preservative | 0.1-20 | 1-15 | 2-10 |
| Fragrance | 0-10 | 0-10 | 0.1-10 |
| Additional Optional Ingredients | 0-15 | 0-15 | 0.1-10 |

TABLE 2D

| Ingredients | First Exemplary Embodiment (wt. %) | Second Exemplary Embodiment (wt. %) | Third Exemplary Embodiment (wt. %) |
| --- | --- | --- | --- |
| Benzalkonium Chloride | 0.3-25 | 0.5-15 | 1-10 |
| Primary Foaming Agent | 3-50 | 4-45 | 5-40 |
| Secondary Foaming Agent | 1-30 | 4-25 | 8-20 |
| Carrier | 0-82.8 | 0-80 | 0-79.8 |
| Foam Structure Enhancing Agent | 0.5-40 | 1-30 | 1-10 |
| Humectant | 3-30 | 3-15 | 3-10 |
| Chelant | 0.1-10 | 0.5-5 | 1-4 |
| Emollient | 0-10 | 0.5-7.5 | 1-5 |
| Preservative | 0.1-20 | 1-15 | 2-10 |
| Fragrance | 0-10 | 0-10 | 0.1-10 |
| Additional Optional Ingredients | 0-15 | 0-15 | 0.1-10 |

TABLE 2E

| Ingredients | First Exemplary Embodiment (wt. %) | Second Exemplary Embodiment (wt. %) | Third Exemplary Embodiment (wt. %) |
| --- | --- | --- | --- |
| Benzethonium Chloride | 0.3-25 | 0.5-15 | 1-10 |
| Primary Foaming Agent | 3-50 | 4-45 | 5-40 |
| Secondary Foaming Agent | 1-30 | 4-25 | 8-20 |
| Carrier | 0-82.8 | 0-80 | 0-79.8 |
| Foam Structure Enhancing Agent | 0.5-40 | 1-30 | 1-10 |
| Humectant | 0.5-30 | 1-15 | 1-10 |
| Chelant | 0.1-10 | 0.5-5 | 1-4 |
| Emollient | 0-10 | 0.5-7.5 | 1-5 |
| Preservative | 0.1-20 | 1-15 | 2-10 |
| Fragrance | 0-10 | 0-10 | 0.1-10 |
| Additional Optional Ingredients | 0-15 | 0-15 | 0.1-10 |

TABLE 2F

| Ingredients | First Exemplary Embodiment (wt. %) | Second Exemplary Embodiment (wt. %) | Third Exemplary Embodiment (wt. %) |
| --- | --- | --- | --- |
| Chlorhexidene Gluconate | 0.3-25 | 0.5-15 | 1-10 |
| Primary Foaming Agent | 3-50 | 4-45 | 5-40 |
| Secondary Foaming Agent | 1-30 | 4-25 | 8-20 |
| Carrier | 0-82.8 | 0-80 | 0-79.8 |
| Foam Structure Enhancing Agent | 0.5-40 | 1-30 | 1-10 |
| Humectant | 0.5-30 | 1-15 | 1-10 |
| Chelant | 0.1-10 | 0.5-5 | 1-4 |
| Emollient | 0-10 | 0.5-7.5 | 1-5 |
| Preservative | 0.1-20 | 1-15 | 2-10 |
| Fragrance | 0-10 | 0-10 | 0.1-10 |
| Additional Optional Ingredients | 0-15 | 0-15 | 0.1-10 |

TABLE 2G

| Ingredients | First Exemplary Embodiment (wt. %) | Second Exemplary Embodiment (wt. %) | Third Exemplary Embodiment (wt. %) |
|---|---|---|---|
| Didecyldimethylammonium chloride | 0.3-25 | 0.5-15 | 1-10 |
| Primary Foaming Agent | 3-50 | 5-45 | 7-40 |
| Secondary Foaming Agent | 1-30 | 4-25 | 8-20 |
| Carrier | 0-82.8 | 0-80 | 0-79.8 |
| Foam Structure Enhancing Agent | 0.5-40 | 1-30 | 1-10 |
| Humectant | 0.5-30 | 1-15 | 1-10 |
| Chelant | 0.1-10 | 0.5-5 | 1-4 |
| Emollient | 0-10 | 0.5-7.5 | 1-5 |
| Preservative | 0.1-20 | 1-15 | 2-10 |
| Fragrance | 0-10 | 0-10 | 0.1-10 |
| Additional Optional Ingredients | 0-15 | 0-15 | 0.1-10 |

The antimicrobial compositions described herein provide a -cidal effect against microorganisms. In a preferred embodiment, the antimicrobial compositions provide a $Log_{10}$ reduction in microorganisms, including, but not limited to bacteria (gram positive and/or negative) and/or fungi, of greater than about 2.5 in about 30 seconds or less; more preferably greater than or equal to about 2.75 in about 30 seconds or less; most preferably greater than or equal to about 3 in about 30 seconds or less when tested according to ASTM E2315 Standard Guide for Assessment of Antimicrobial Activity Using a Time Kill Procedure.

While an understanding of the mechanism is not necessary to practice the present invention and while the present invention is not limited to any particular method of preparation, it is contemplated that, in some embodiments, the compositions can be prepared by combining the ingredients and mixing them until a homogeneous or near homogeneous mixture is prepared.

When provided as a liquid concentrate composition, the concentrate can be diluted through dispensing equipment using aspirators, peristaltic pumps, gear pumps, mass flow meters, and the like. This liquid concentrate embodiment can also be delivered in bottles, jars, dosing bottles, bottles with dosing caps, and the like. The liquid concentrate composition can be filled into a multi-chambered cartridge insert that is then placed in a spray bottle or other delivery device filled with a pre-measured amount of water.

The carrier used to dilute the concentrate will often be water or a water miscible carrier. When water is used, it can be available at the locale or site of dilution. In this respect, water for dilution may contain varying levels of hardness depending upon the locale. Service water available from various municipalities have varying levels of hardness. It is desirable to provide a concentrate that can handle the hardness levels found in the service water of various municipalities. The water of dilution that is used to dilute the concentrate can be characterized as hard water when it includes at least 1 grain hardness. It is expected that the water of dilution can include at least 5 grains hardness, at least 10 grains hardness, or at least 20 grains hardness.

It is expected that the concentrate will be diluted with the carrier in order to provide a use solution having a desired level of concentration of active ingredients. Preferably the concentrate can be diluted with the carrier at a weight ratio of at least about 1:1 and up to about 1:25.

In an alternate embodiment, the cleaning compositions may be provided as a ready-to-use ("RTU" or "use") composition. If the cleaning composition is provided as a RTU composition, a more significant amount of carrier is added to the cleaning composition as a diluent. It may be desirable to provide the concentrate (liquid or gel) in a flowable form so that it can be pumped or aspirated. It has been found that it is generally difficult to accurately pump a small amount of a liquid. It is generally more effective to pump a larger amount of a liquid. Accordingly, although it is desirable to provide the concentrate with as little carrier as possible in order to reduce transportation costs, it is also desirable to provide a concentrate that can be dispensed accurately.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following examples are provided herein:

Cocoyl Methyl Glucamide: a glucosamide surfactant, used as a foaming agent, sold as GlucoTain Care by Clariant.

Cocamidopropyl Betaine: a non-ionic surfactant, used as a foaming agent.

Coco Glucoside: a non-ionic surfactant, used as a foaming agent.

Cocamine Oxide: a non-ionic surfactant, used as a foaming agent.

Palmitamidopropyl Trimonium Chloride: a cationic surfactant, used as a foaming agent.

Benzalkonium Choride: an antimicrobial agent.

Capryloyl/Caproyl Methyl Glucamide: a glucosamide surfactant, used as a foaming agent, sold as GlucoTain Clear by Clariant.

Cetrimonium Chloride: a cationic surfactant and foaming agent.

Soyethyl Morpholinium Ethosulfate: a cationic surfactant and foaming agent.

Soyamidopropyl Ethyldimonium Ethosulfate: a cationic surfactant and foaming agent Propylene Glycol: a humectant.

Cocotrimonium Methosulfate: a cationic surfactant and foaming agent.

Isostearyl Ethylimidazolinium Ethosulfate: a cationic surfactant and foaming agent.

Linoleamidopropyl Ethyldiamonium Ethosulfate: a cationic surfactant and foaming agent.

Ricinoleamidopropyl Ethyldimonium Ethosulfate: a cationic surfactant and foaming agent.

Cocamidopropyl PG-Dimonium Chloride Phosphate: a foaming agent.

Lauryl Trimethyl Ammonium Chloride: a foaming agent.

Glycerin: a humectant.

Phenoxyethanol: a preservative.

Hexylene Glycol: a coupling agent.

Methyl Gluceth 20: a humectant.

Methylglycinediacetic Acid: a chelant.

Hydroxyethylcellulose, a thickening agent

Citric Acid: used to adjust pH.

Potassium Hydroxide: used to adjust pH.

Water: used as a carrier.

Multiple commercially available antimicrobial foaming hand soaps were tested for comparative purposes. Those included a commercially available 0.55 active % benzalkonium chloride and amine oxide antimicrobial hand soap, a 0.2 active % benzalkonium chloride and cationic surfactant antimicrobial hand soap, and a 4 active % chlorhexidine gluconate antimicrobial hand soap.

In Examples 1-4, the survival of challenged organisms exposed to an antimicrobial test composition was measured using in vitro Time Kill testing, based on ASTM E 2315 Standard Guide for Assessment of Antimicrobial Activity Using a Time Kill Procedure. Utilizing this method, the inoculum is prepared by growing a microbial culture using a D/E agar medium. The microbial population then is washed from the agar with sterile physiological saline and the population of the microbial suspension is adjusted to around $10^8$ colony forming units (cfu) per ml. An aliquot of the test formula, or a dilution thereof, is brought into contact with this known population of bacteria at ambient temperature. The test composition is neutralized after a set amount of time, which arrests the antimicrobial activity of the test sample. The log reduction from the original bacteria population is calculated using the following formula:

$\log_{10}$ reduction=$\log_{10}$(control)−$\log_{10}$(test sample survivors)

Each test was performed in duplicate and the average log reduction reported.

Example 1

The efficacy of formulations with differing cationic-compatible surfactants with the same alkyl chain length is outlined in Tables 3 and 4. In each instance, citric acid and/or potassium hydroxide were used to maintain a pH of 6, and water was added quantum satis.

The formula containing cocoyl methyl glucamide exhibits antimicrobial activity equivalent to the formula containing cocamine oxide alone and in a blend of the two surfactants. The culture used was *Staphylococcus aureus* ATCC 6538, a Gram-positive bacterium.

TABLE 3

Impact of primary foaming agents on Microbiological Efficacy

| | A | B | C |
|---|---|---|---|
| | | Weight % | |
| Cocoyl Methyl Glucamide | 0 | 0.5 | 1 |
| Hydroxyethyl cellulose | 0.05 | 0.05 | 0.05 |
| Cocamine Oxide | 1 | 0.5 | 0 |
| Cetyl Trimonium Chloride | 1 | 1 | 1 |
| Benzalkonium Chloride | 0.2 | 0.2 | 0.2 |
| Ph | 6.2 | 6.2 | 6.2 |
| *E. coli* Time Kill efficacy ($\log_{10}$ Reduction, 30 seconds) | >5.53 | >5.53 | >5.53 |

TABLE 4

Impact of Several Classes of Cationic-Compatible Surfactants on Microbiological Efficacy

| | 1A | 1B | 1C | 1D |
|---|---|---|---|---|
| | | Weight % | | |
| Cocoyl Methyl Glucamide | 1 | 0 | 0 | 0 |
| Cocamidopropyl Betaine | 0 | 1 | 0 | 0 |
| Coco Glucoside | 0 | 0 | 1 | 0 |
| Cocamine Oxide | 0 | 0 | 0 | 1 |
| Palmitamidopropyl Trimonium Chloride | 1 | 1 | 1 | 1 |
| Benzalkonium Chloride | 0.2 | 0.2 | 0.2 | 0.2 |
| pH | 6 | 6 | 6 | 6 |
| *E. coli* Time Kill efficacy ($\log_{10}$ Reduction, 30 seconds) | >5.74 | 2.01 | 4.48 | >5.74 |

All surfactant classes tested in Tables 3 and 4 were chemically compatible with cationic active ingredients. Despite this chemical compatibility, cocamidopropyl betaine had a significant negative impact on microbiological efficacy. Coco glucoside also had a negative impact on microbiological efficacy, which is surprising given its high degree of structural similarity to cocoyl methyl glucamide. The formula containing cocoyl methyl glucamide exhibits antimicrobial activity equivalent to the formula containing cocamine oxide. The culture used was *Escherichia coli* ATCC 11229, a Gram-negative bacterium.

As can be seen in Tables 3 and 4, the glucamide provided substantially similar $\log_{10}$ reduction to the amine oxide, or in a mixture with amine oxide, both producing a reduction of greater than 5.74 $\log_{10}$ at 30 seconds contact time for *Escherichia coli* and greater than 5.53 $\log_{10}$ at 30 seconds contact time for *Staphylococcus aureus*.

Example 2

Various cationic surfactants were evaluated for their ability to enhance foam volume and quality, while maintaining antimicrobial efficacy. In each instance, citric acid and/or potassium hydroxide were used to maintain a pH of 5.7-6, and water was added quantum satis. The culture used was *Staphylococcus aureus* ATCC 6538, a Gram-positive bacterium. To dilute the samples, 1 ml of product was combined with 9 ml of lab-purified water.

Results are outlined in Table 5. Foam quality was determined by applying one pump of the product onto hands and performing a 30 second hand wash. Ratings were based on visual comparison to a standard set of photographs that defined each rating. The scale ranges from 1 (poor) to 5 (best).

TABLE 5

Screening Evaluation of Numerous Cationic Surfactants

| | | 2A | 2B | 2C | 2D | 2E | 2F | 2G | 2H |
|---|---|---|---|---|---|---|---|---|---|
| | | | | | Weight % | | | | |
| Active (Antimicrobial) | Benzalkonium Chloride | 0.2 | 0.2 | 0.2 | 0.2 | 0.2 | 0.2 | 0.2 | 0.2 |
| Nonionic surfactant | Caproyloyl/Caproyl Methyl Glucamide | 1.5 | 1.5 | 1.5 | 1.5 | 1.5 | 1.5 | 1.5 | 1.5 |
| Cationic Surfactant | Cetrimonium Chloride | 0 | 0 | 0 | 1.3 | 0 | 0 | 0 | 0 |
| Cationic Surfactant | Soyethyl Morpholinium Ethosulfate | 0 | 0 | 0 | 0 | 0 | 0 | 0 | 1.3 |
| Cationic Surfactant | Palmitamidopropyltrimonium Chloride | 0 | 0 | 1.3 | 0 | 0 | 0 | 0 | 0 |
| Cationic Surfactant | Soyamidopropyl Ethyldimonium Ethosulfate (and) Propylene Glycol | 1.3 | 0 | 0 | 0 | 0 | 0 | 0 | 0 |
| Cationic Surfactant | Cocotrimonium Methosulfate | 0 | 1.3 | 0 | 0 | 0 | 0 | 0 | 0 |
| Cationic Surfactant | Isostearyl Ethylimidazolinium Ethosulfate (and) Propylene Glycol | 0 | 0 | 0 | 0 | 1.3 | 0 | 0 | 0 |
| Cationic Surfactant | Linoleamidopropyl Ethyldiamonium Ethosulfate | 0 | 0 | 0 | 0 | 0 | 1.3 | 0 | 0 |
| Cationic Surfactant | Ricinoleamidopropyl Ethyldimonium Ethosulfate | 0 | 0 | 0 | 0 | 0 | 0 | 1.3 | 0 |
| | pH | 6 | 6 | 6 | 6 | 6 | 6 | 6 | 6 |
| | Staph $Log_{10}$ Reduction 30 Seconds (Undiluted) | <0.5 | >5.44 | <0.5 | >5.44 | >5.44 | <0.5 | <0.5 | <0.5 |
| | Staph $Log_{10}$ Reduction 30 Seconds (10% Dilution) | <0.5 | 3.02 | <0.5 | 2.97 | 1.98 | <0.5 | <0.5 | 2.19 |
| | Foam Quality Rating | 3.5 | 3.5 | 4 | 3.5 | 2 | 3 | 2.5 | 2 |

As can be seen in Table 5, it was found that formulas containing either cetrimonium chloride or cocotrimonium methosulfate had the highest microbiological efficacy. These surfactants have short average alkyl chain lengths (between about 10 and about 14 carbons). It was found that longer alkyl chain lengths had an inhibitory effect on microbiological efficacy. Thus, preferably, the primary foaming agent has a carbon chain length of about 18 or less carbons; more preferably about 16 or less; most preferably between about 10 and 14 carbons. These surfactants also produced acceptable foam, with a foam quality rating of 3.5.

Once it was determined that cationic surfactants with chain lengths having 18 or less carbons provided enhanced microbiological efficacy, three such cationic surfactants were evaluated against *Serratia marcescens*, a Gram negative microorganism. That data is provided in Table 6.

TABLE 6

Evaluation of Shorter Chain Length Cationic Surfactants

| | 3A | 3B | 3C |
|---|---|---|---|
| Cocamine Oxide | 1.2 | 1.2 | 1.2 |
| Benzalkonium Chloride | 0.6 | 0.6 | 0.6 |
| Laurtrimonium Chloride | 1.2 | 0 | 0 |
| Palmitamidopropyl trimonium chloride | 0 | 1.2 | 0 |
| Cocotrimonium methosulfate | 0 | 0 | 1.2 |
| Log10 Reduction* | >3.79 | 1.62 | 2.17 |

*Serratia marcescens, 30 seconds

As can be seen in Table 6, Laurtrimonium chloride demonstrated the highest degree of efficacy; notably it had the shortest alkyl chain length with 12 carbons. Palmitamidopropyl trimonium chloride had the longest average alkyl chain length with between 14 and 16 carbons and showed the lowest degree of microbiological efficacy.

Example 3

Table 7 summarizes the efficacy of laurtrimethylammonium chloride ("LTAC") compared to cocotrimonium methosulfate for the gram-negative organism *Serratia marcescens* ATCC 14756.

TABLE 7

Efficacy of Cationic Surfactants while Varying the Concentration of the Antimicrobial Active Ingredient

| | Weight % (As active material) | | | | |
|---|---|---|---|---|---|
| | 4A | 4B | 4C | 4D | 4E |
| Capryloyl/Caproyl Methyl Glucamide | 0.05-1.5 | 0.05-1.5 | 0.05-1.5 | 0.05-1.5 | 0.05-1.5 |
| Cocamidopropyl PG-Dimonium Chloride Phosphate | 0.1-3 | 0.1-3 | 0.1-3 | 0.1-3 | 0.1-3 |
| Benzalkonium Chloride | 0.1 | 0.2 | 0.6 | 1 | 0.2 |
| Palmitamidopropyl Trimonium chloride | 0.1-3 | 0.1-3 | 0.1-3 | 0.1-3 | 0.1-3 |
| Laurtrimethyl Ammonium chloride | 0.5-3 | 0.5-3 | 0.5-3 | 0.5-3 | 0 |
| Cocotrimonium Methosulfate | 0 | 0 | 0 | 0 | 0.5-3 |
| Glycerin | 0.05-1.5 | 0.05-1.5 | 0.05-1.5 | 0.05-1.5 | 0.05-1.5 |
| Phenoxyethanol | 0.1-1.5 | 0.1-1.5 | 0.1-1.5 | 0.1-1.5 | 0.1-1.5 |
| Hexylene Glycol | 0.5-3 | 0.5-3 | 0.5-3 | 0.5-3 | 0.5-3 |
| Methyl Gluceth 20 | 0.05-1.5 | 0.05-1.5 | 0.05-1.5 | 0.05-1.5 | 0.05-1.5 |
| Methylglycinediacetic acid | 0.05-1 | 0.05-1 | 0.05-1 | 0.05-1 | 0.05-1 |
| pH | 5-8 | 5-8 | 5-8 | 5-8 | 5-8 |
| Antimicrobial Efficacy | | | | | |
| *S. marcescens* Efficacy (Log$_{10}$ Reduction, 30 Seconds) | 3.2 | 5.11 | 5.11 | >4.3 | 1.7 |

As can be seen in Table 7, the formulations including laurtrimethylammonium chloride provided better antimicrobial properties than the formula containing cocotrimonium methosulfate. Formula 4B and 4E contain the same ingredients at the same levels. The only difference between the formulas is that Formula 4B contains 1.2% of the cationic surfactant lauryltrimethyl ammonium chloride whereas Formula 4E contains 1.2% of the cationic surfactant cocotrimonium methosulfate. Formula 4B showed nearly a 3.5 Log enhancement in efficacy compared to Formula 4E. Formulas 4A thru 4D demonstrate that formulas with active antimicrobial levels ranging from 0.1% to 1.0% show high antimicrobial efficacy. It was observed that formulations providing the best -cidal effect were included the lauryltrimethylammonium chloride in combination with between about 0.2 wt. % and about 1 wt. % benzalkonium chloride.

Example 4

The effectiveness of formulas 4B and 4C, detailed in Table 9, were compared with two current commercially available hand soaps—a quaternary ammonium and 0.55% benzalkonium antimicrobial hand soap with an amine oxide-based surfactant system, and a 0.2% benzalkonium chloride antimicrobial hand soap. The cultures used were: Gram-negative *Serratia marcescens* ATCC 14756, Gram-positive *Staphylococcus aureus* (MRSA) ATCC 33592, and Gram-negative *Escherichia coli* ATCC 10708. To more closely simulate the soil present on hands in a clinical simulation hand wash study, the test products were diluted with 9 parts tryptic soy broth to 1 part test product immediately prior to testing. The results of the comparative testing are displayed in Table 9, where the commercially available formulations showed minimal antimicrobial effects.

TABLE 8

Preferred Antibacterial Formulations.

| | Weight % | |
|---|---|---|
| | 4B | 4C |
| Capryloyl/Caproyl Methyl Glucamide | 0.05-1.5 | 0.05-1.5 |
| Cocamidopropyl PG-Dimonium Chloride Phosphate | 0.1-3 | 0.1-3 |
| Benzalkonium Chloride | 0.2 | 0.6 |
| Palmitamidopropyl Trimonium Chloride | 0.1-3 | 0.1-3 |
| Lauryl Trimethyl Ammonium Chloride | 0.5-3 | 0.5-3 |
| Glycerin | 0.05-1.5 | 0.05-1.5 |
| Phenoxyethanol | 0.1-1.5 | 0.1-1.5 |
| Hexylene Glycol | 0.5-3 | 0.5-3 |
| Methyl Gluceth 20 | 0.05-1.5 | 0.05-1.5 |
| Methylglycinediacetic acid | 0.05-1 | 0.05-1 |

TABLE 9

Efficacy of Preferred Formulas and Competitive Products.

| | Microbiological Efficacy (Log$_{10}$ Reduction, 30 seconds) | | |
|---|---|---|---|
| Formula | *Serratia marcescens* | *S. aureus* (MRSA) | *E. coli* |
| 4B | 5.11 | >5.79 | >5.51 |
| 4C | 5.11 | >5.79 | >5.51 |
| Benzalkonium Chloride (0.55%) Amine Oxide Hand Soap | 1.52 | 0.56 | 0.60 |
| Benzalkonium Chloride (0.2%) & cationic surfactant Hand Soap | 0.23 | 0.93 | 0.13 |

As can be seen in Table 9, the two exemplary formulas of the invention significantly outperformed the two commercially available antimicrobial foaming hand soaps. The two exemplary formulas provided greater than a 5-Log$_{10}$ reduction of the three bacteria tested.

The next best $Log_{10}$ reduction from the commercially available products was 1.52.

Example 5

Testing was performed to assess performance of differing chelants. Multiple amino acid based chelants were tested in exemplary compositions of the invention and tested against a control formulation containing no chelant. The formulations are provided in Table 10.

TABLE 10

|  | 5A | 5B | 5C |
|---|---|---|---|
|  | Weight % (as active material) | | |
| Capryloyl/Caproyl Methyl Glucamide | 0.05-1.5 | 0.05-1.5 | 0.05-1.5 |
| Cocamidopropyl PG-Dimonium Chloride Phosphate | 0.1-3 | 0.1-3 | 0.1-3 |
| Benzalkonium Chloride | 0.1-1 | 0.1-1 | 0.1-1 |
| Palmitamidopropyl Trimonium chloride | 0.1-3 | 0.1-3 | 0.1-3 |
| Cocotrimonium Methosulfate | 0.5-3 | 0.5-3 | 0.5-3 |
| Glycerin | 0.05-1.5 | 0.05-1.5 | 0.05-1.5 |
| Phenoxyethanol | 0.1-1.5 | 0.1-1.5 | 0.1-1.5 |
| Hexylene Glycol | 0.5-3 | 0.5-3 | 0.5-3 |
| Methyl Gluceth 20 | 0.05-1.5 | 0.05-1.5 | 0.05-1.5 |
| GLDA | 0 | 0.05-1 | 0 |
| MGDA | 0 | 0 | 0.05-1 |

Formula 5A served as the control having no chelant. Formulas 5B and 5C included GLDA and MGDA, respectively, for comparative testing against each other and the control. The compositions were inoculated with *Serratia marcescens* ATCC 14756 for 30 seconds at room temperature. Before adding the antimicrobial compositions, the inoculum numbers were measured (CFO/mL). The average count was $1.2 \times 10^7$ CFU/mL providing a log average of 8.06. The results of the testing are shown below in Table 11. The inoculated surface was contacted with the various formulations for 30 seconds and the log reduction was measured.

TABLE 11

| Time Kill Efficacy *Serratia Marcescens* | |
|---|---|
| Formula | Log Reduction |
| 5A | <1.0 |
| 5B | <1.0 |
| 5C | 6.1 |

Thus, it was found that MGDA provided unexpectedly surprising results having much higher log reduction than the structurally similar GLDA in the tested compositions.

Example 6

The foaming characteristics of an exemplary formulation of the antimicrobial hand wash compositions described herein was compared to the foaming characteristics of commercially available antimicrobial hand wash products with cationic active ingredients.

The exemplary formulation is provided in Table 12

TABLE 12

| Exemplary Hand Wash Formula 6 | |
|---|---|
|  | Weight % |
| Capryloyl/Caproyl Methyl Glucamide | 0.05-1.5 |
| Cocamidopropyl PG-Dimonium Chloride Phosphate | 0.1-3 |
| Benzalkonium Chloride | 0.1-1 |
| Palmitamidopropyl Trimonium Chloride | 0.1-3 |
| Lauryl Trimethyl Ammonium Chloride | 0.5-3 |
| Glycerin | 0.05-1.5 |
| Phenoxyethanol | 0.1-1.5 |
| Hexylene Glycol | 0.05-3 |
| Methyl Gluceth 20 | 0.05-1.5 |
| Methylglycinediacetic acid | 0.05-1 |
| Hydroxyethylcellulose | 0.01-0.1 |

Exemplary Formula 6 (shown in Table 12) was compared with two exemplary commercially available hand was compositions. To evaluate the foaming characteristics formulas were diluted by adding 90 mL of deionized water to 10 mL of test formula. 40 mL of diluted test formula was added to a 250-mL graduated cylinder. Cylinders were rotated at 30 RPM for 4 minutes. The foam volume is determined by immediately recording the volume based on graduated cylinder markings. Four replicates were evaluated for each test material. Presented in Table 13 are the average of the four measurements.

TABLE 13

| Test Formula | Active Ingredient | Foam Height (mL) |
|---|---|---|
| Commercial Product A | 4% CHG | 158.50 |
| Commercial Product B | 0.18% Benzalkonium Chloride | 186.25 |
| Formula 6 | 0.6% Benzalkonium Chloride | 206.50 |

As can be seen in Table 13, Formula 6 provided more foam than commercially available products.

Example 7

After demonstrating the in vitro activity of exemplary formulas and the superior foaming characteristics compared to commercially available products, tests were performed to assess the in vivo efficacy of an exemplary formulation of a hand soap of the invention in a human clinical hand wash study. The exemplary formula of the inventive handsoap was Formula 6 (provided in Table 12). This was tested against a commercially available 0.2% benzethonium chloride antimicrobial hand soap ("Commercial A"), a commercially available 0.5% benzalkonium chloride antimicrobial hand soap ("Commercial B"), a commercially available 0.55% benzalkonium chloride antimicrobial hand soap ("Commercial C"), a commercially available 2% chlorhexidine gluconate antimicrobial hand soap ("Commercial D"), and a commercially available 4% chlorhexidine gluconate antimicrobial hand soap ("Commercial D"). The culture used was *Serratia marcescens* ATCC 14756, a Gram-negative bacterium. The test was performed ASTM E1174 Standard Test Method for Evaluation of the Effectiveness of Health Care Personnel Handwash Formulations. The results of the testing are provided Table 14 below and depicted in the FIGURE.

TABLE 14

Human Clinical Efficacy Study Results

| Formula | Active Ingredient | Microbiological Efficacy ($Log_{10}$ Reduction) |
|---|---|---|
| Commercial A | 0.20% Benzethonium Chloride | 2.35 |
| Commercial B | 0.50% Benzalkonium Chloride | 2.42 |
| Commercial C | 0.55% Benzalkonium Chloride | 2.32 |
| Formula 6 | 0.55% Benzalkonium Chloride | 3.03 |
| Commercial D | 2% Chlorhexidine Gluconate | 2.93 |
| Commercial E | 4% Chlorhexidine Gluconate | 3.07 |

As can be seen from the data in Table 14 and the FIGURE, the exemplary formulation provided a $Log_{10}$ reduction of 3.03, which is not statistically significantly different from the antimicrobial efficacy observed from the 4% chlorhexidine gluconate commercially available antimicrobial hand soap that provided a $Log_{10}$ reduction of 3.07, which is surprising given the significant difference in the active concentration of the cationic active antimicrobial ingredient. Further, the exemplary formulation produced better -cidal effect than all of the other comparative commercial products tested.

Thus, this data provides a surprising result, i.e., that 0.55% label active concentration of the antimicrobial active ingredient in the compositions of the invention can perform substantially similarly to 4% active CHG. Thus, substantially similar efficacy was obtained with about one eighth of the active concentration, which was unexpected.

Overall, we have described an antimicrobial hand soap with significantly enhanced efficacy compared to currently available benzalkonium chloride-based handsoaps. Despite avoiding traditional high foaming surfactant classes, we were also able to demonstrate improved foaming characteristics compared to currently available cationic active-based antimicrobial handsoaps. Finally, we were able to employ the use of mild surfactants with skin conditioning properties.

Example 8

Further testing was performed to assess the stability of the compositions in concentrated form and their retention of antimicrobial properties when prepared in concentrated form and diluted to a use composition. A concentrated hand wash composition was prepared according to Table 15 (a concentration of about 10×). The concentrated formula was diluted by adding 9 parts water to 1 part concentrated formula to produce the use solution for antimicrobial efficacy testing.

TABLE 15

| | |
|---|---|
| Capryloyl/Caproyl Methyl Glucamide | 05-10 |
| Cocamidopropyl PG-Dimonium Chloride Phosphate | 2-7 |
| Glyceryl Caprylate/Caprate | 7-13 |
| Alkyl Dimethyl Benzyl Ammonium Chloride | 0.5-5 |
| 1,2-propylene glycol | 0.5-5 |
| Lauryl Trimethyl Ammonium Chloride | 3-7 |
| Glycerin | 3-7 |
| Phenoxyethanol | 0.5-2 |
| Hexylene Glycol | 3-8 |
| Methyl Gluceth 20 | 0.5-5 |
| MGDA | 0.5-2 |
| Water | Q.S. |

The use solution was then tested against *S. marcescens* in a time kill test. The composition provided a $Log_{10}$ Reduction of 4.19 after 30 second exposure time. This demonstrated that the compositions could be prepared as stable concentrated formulations and later diluted to use solutions that retain their antimicrobial efficacy.

The inventions being thus described, it will be obvious that the same may be varied in many ways. Such variations are not to be regarded as a departure from the spirit and scope of the inventions. Since many embodiments can be made without departing from the spirit and scope of the invention, the invention resides in the claims.

What is claimed is:

1. An antimicrobial composition comprising:
    from about 0.01 wt. % to about 2 wt. % of an antimicrobial active compound comprising one or more of the following benzalkonium chloride, benzethonium chloride, chlorhexidine gluconate, and mixtures thereof, wherein the antimicrobial active compound has antimicrobial activity toward Gram positive and/or Gram negative microorganisms;
    from about 0.1 wt. % to about 5 wt. % of a primary foaming agent, wherein the primary foaming agent comprises a glucosamide or a mixture of a glucosamide and a C8-C16 amine oxide derivative in a ratio of between about 90:10 and about 50:50; and
    from about 65 wt. % to about 99.7 wt. % of a carrier;
    wherein the composition is a liquid or a gel and has a pH between about 5 and about 9;
    wherein the antimicrobial composition provides an in vitro log reduction of the microorganisms of greater than or equal to 3 in about 30 seconds or less.

2. The antimicrobial composition of claim 1, wherein the primary foaming agent is a C8-C16 glucosamide and the composition contains less than 1 wt. % amine oxide.

3. The antimicrobial composition of claim 1, wherein the composition further comprises a secondary foaming agent in a concentration between about 0.1 wt. % and about 5 wt. %.

4. The antimicrobial composition of claim 1, wherein the composition further comprises a chelant comprising methylglycinediacetic acid in a concentration between about 0.01 wt. % and about 1 wt. %.

5. The antimicrobial composition of claim 1, wherein the composition further comprises a foam structure enhancing agent in a concentration between about 0.05 wt. % and about 3 wt. %.

6. The antimicrobial composition of claim 1, wherein the composition further comprises a humectant in a concentration between about 0.05 wt. % and about 1 wt. %.

7. The antimicrobial composition of claim 1, wherein the composition further comprises a preservative in a concentration between about 0.1 wt. % and about 2 wt. %.

8. The antimicrobial composition of claim 1, wherein the composition further comprises an emollient in a concentration between about 0.01 wt. % and about 1 wt. %.

9. The antimicrobial composition of claim 2, wherein the primary foaming agent comprises a C8-C16 glucosamide, and wherein the C8-C16 glucosamide comprises capryloyl/caproyl methyl glucosamide, cocoyl methyl glucosamide, lauroyl/myristoyl methyl glucamide, or a mixture thereof.

10. The antimicrobial composition of claim 3, wherein the composition further comprises a secondary foaming agent, which comprises trimethyl ammonium chloride, palmitamidopropyl trimonium chloride, a phospholipid surfactant, a phospholipid derivative surfactant, or mixtures thereof.

11. The antimicrobial composition of claim 1, wherein the composition provides a log reduction of *S. marcescens* of greater than about 4 in about 30 seconds in an in vitro assay.

12. The antimicrobial composition of claim 1, wherein the composition further comprises one or more additional functional ingredients.

13. The antimicrobial composition of claim 1, wherein the composition is a liquid.

14. A dilutable antimicrobial composition comprising:
   from about 0.3 wt. % to about 25 wt. % of an antimicrobial active compound comprising one or more of the following benzalkonium chloride, benzethonium chloride, chlorhexidine gluconate, didecyldimethylammonium chloride and mixtures thereof, wherein the antimicrobial active compound has antimicrobial activity toward Gram positive and/or Gram negative microorganisms;
   from about 3 wt. % to about 50 wt. % of a primary foaming agent, wherein the primary foaming agent comprises a glucosamide or a mixture of a glucosamide and a C8-C16 amine oxide derivative in a ratio of between about 90:10 and about 50:50; and
   optionally from about 0 wt. % to about 96.5 wt. % of a carrier; wherein the composition is a liquid or a gel and has a pH between about 5 and about 9;
   wherein the antimicrobial composition provides an in vitro log reduction of the microorganisms of greater than or equal to 3 in about 30 seconds or less.

15. The antimicrobial composition of claim 14, wherein the primary foaming agent is a C8-C16 glucosamide and the composition contains less than 1 wt. % amine oxide.

16. The antimicrobial composition of claim 15, wherein the composition further comprises a secondary foaming agent in a concentration between about 1 wt. % and about 30 wt. %.

17. The antimicrobial composition of claim 16, wherein the composition further comprises a chelant comprising methylglycinediacetic acid in a concentration between about 0.1 wt. % and about 10 wt. %.

18. The antimicrobial composition of claim 17, wherein the composition further comprises a foam structure enhancing agent in a concentration between about 0.5 wt. % and about 35 wt. %.

19. The concentrated antimicrobial composition of claim 18, wherein the composition is diluted at a dilution ratio between 1:5 and 1:15 to form a ready to use antimicrobial hand soap.

20. A method of preparing the antimicrobial composition of claim 1 comprising:
   (a) mixing the ingredients of the composition.

21. The method of claim 20, wherein the composition is mixed until homogenous.

22. The method of claim 21, wherein the method further comprises diluting the composition.

* * * * *